United States Patent

Sorger et al.

(10) Patent No.: US 6,506,942 B2
(45) Date of Patent: Jan. 14, 2003

(54) PROCESS FOR THE PREPARATION OF CARBONYL COMPOUNDS BY CLEAVAGE OF HYDROXYCARBOXYLIC ACIDS

(75) Inventors: Klas Sorger, Munich; Hermann Petersen, Burghausen; Juergen Stohrer, Pullach, all of (DE)

(73) Assignee: Consortium Fur Elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/976,988

(22) Filed: Oct. 12, 2001

(65) Prior Publication Data

US 2002/0077498 A1 Jun. 20, 2002

(30) Foreign Application Priority Data

Dec. 14, 2000 (DE) .......................... 100 62 178

(51) Int. Cl.⁷ ............................... C07C 45/00
(52) U.S. Cl. ................ 568/314; 568/385; 568/397; 568/402; 568/404
(58) Field of Search ................ 568/314, 316, 568/318, 319, 385, 397, 402, 404

(56) References Cited

U.S. PATENT DOCUMENTS 5,274,136 A * 12/1993 Mills et al.
5,750,795 A * 5/1998 Saito

FOREIGN PATENT DOCUMENTS

WO 96/15142 5/1996

OTHER PUBLICATIONS

D. Ivanoff, Bull. Soc. Chem. France 36, 321 (1933).
C.S. Rondestredt, M.E. Rowley, J. Am. Chem. Soc. 78, 3804 (1956).
K.S. Fors, J.R. Gage, R.F. Heier, R.C. Kelly, W.R. Perrault, N. Wienienski, J. Org. Chem. 63, 7348 (1998).

* cited by examiner

Primary Examiner—James O. Wilson
Assistant Examiner—Sikarl A. Witherspoon

(57) ABSTRACT

The invention relates to a process for the preparation of a carbonyl compound of the general formula (1)

$$R^1R^2C=O \qquad (1),$$

in which a β-hydroxycarboxylic acid or its salt of the general formula (2)

$$R^1R^2C(OH)-CR^3R^4-COOM \qquad (2)$$

is cleaved in the presence of a Brönstedt base which is selected from hydroxides, alkanolates, oxides, amides and hydrides of the alkali metals and alkaline earth metals, and in the presence of a hydroxyl-free solvent, $R^1$, $R^2$, $R^3$, $R^4$ and M having the meanings from claim 1.

20 Claims, No Drawings

PROCESS FOR THE PREPARATION OF CARBONYL COMPOUNDS BY CLEAVAGE OF HYDROXYCARBOXYLIC ACIDS

BACKGROUND OF THE INVENTION

1. Field of the Invention

The invention relates to a process for the preparation of carbonyl compounds by cleavage of hydroxycarboxylic acids in the presence of a Brönstedt base and a hydroxyl-free solvent.

2. Background Art

β-Hydroxycarboxylic esters, β-hydroxycarboxamides and β-hydroxyketones are usually cleaved thermally or under acid or base catalysis into the corresponding carbonyl compounds by retroaldolization (as, for example, in WO 9615142).

For example, the cleavage of di-, tri- and tetrasubstituted β-hydroxypropionic acids in water in the presence of the bases potassium hydroxide or potassium carbonate, in aqueous alcoholic solution in the presence of the base sodium hydroxide, and in 1-propanol in the presence of the base sodium 1-propanolate, is known from D. Ivanoff, BULL. SOC. CHIM. France 36, 321 (1933) and C. S. Rondestvedt, M. E. Rowley, J. AM. CHEM. SOC. 78, 3804 (1956).

The previously known processes have the following disadvantages. In most cases, the cleavage of the β-hydroxypropionic acids takes place incompletely with poor yields by weight. Only in a few cases, when the β-hydroxypropionic acids have aryl groups in the α- and/or β-position, does the cleavage take place completely. In some cases, particularly when the β-hydroxypropionic acids have hydrogen atoms as substituents in the α- and/or β-position, no cleavage occurs. The yield by weight, based on the carbonyl compounds formed during the cleavage, is therefore inevitably reduced in most cases.

Furthermore, the cleavage of the β-hydroxypropionic acids takes place in most cases very slowly and generally requires reaction times of more than 10 h, which makes the reaction very uneconomical, particularly when carried out on an industrial scale, owing to the poor yields as a function of time.

In addition, on working up in an aqueous medium to obtain or isolate the carbonyl compounds of the general formula (2), the water-miscible 1-propanol or other alcohol solvent dissolves in the aqueous phase. For reasons of cost-efficiency and for reducing the amounts of waste, recovery of the solvent used from the aqueous phase (for example by extraction or distillation) is necessary, particularly when used on an industrial scale. Such recovery, however, is associated with considerable cost. In addition, the use of water-immiscible organic solvents, such as ethyl acetate or methyl tert-butyl ether as cosolvents to achieve better phase separation is necessary with the use of water-miscible solvents such as 1-propanol or other alcohols during work-up to obtain or isolate the carbonyl compounds of the general formula (2). These solvents must be recovered and must be freed from impurities by distillation before being reused, which likewise is associated with high cost.

SUMMARY OF THE INVENTION

It is therefore an object of the invention to provide an economical process which makes it possible to cleave β-hydroxycarboxylic acids and to obtain and to isolate, in high yields and purities, the carbonyl compounds formed in the cleavage.

DETAILED DESCRIPTION OF THE PREFERRED EMBODIMENT(S)

The invention relates to a process for the preparation of a carbonyl compound of the general formula (1)

in which a β-hydroxycarboxylic acid or its salt of the general formula (2)

is cleaved in the presence of a Brönstedt base which is selected from hydroxides, alkanolates, oxides, amides, and hydrides of the alkali metals and alkaline earth metals, and a hydroxyl-free solvent, where $R^1$ denotes an optionally halogen- or cyano-substituted $C_1$–$C_{30}$-hydrocarbon radical in which one or more, non-neighboring methylene units may be replaced by groups —O—, —CO—, —COO—, —OCO— or —OCOO—, —S— or —NR$^x$— and in which one or more, non-neighboring methine units may be replaced by groups —N=, —N=N— or —P=, $R^2$ denotes hydrogen or an optionally halogen- or cyano-substituted $C_1$–$C_{30}$-hydrocarbon radical in which one or more, non-neighboring methylene units may be replaced by groups —O—, —CO—, —COO—, —OCO— or —OCOO—, —S— or —NR$^x$— and in which one or more, non-neighboring methine units may be replaced by groups —N=, —N=N— or —P=, $R^3$ and $R^4$ denote hydrogen, halogen or an optionally halogen- or cyano-substituted $C_1$–$C_{30}$-hydrocarbon radical in which one or more, non-neighboring methylene units may be replaced by groups —O—, —CO—, —COO—, —OCO— or —OCOO—, —S— or —NR$^x$— and in which one or more, non-neighboring methine units may be replaced by groups —N=, —N=N— or —P=, $R^x$ denotes hydrogen or an optionally halogen- or cyano-substituted $C_1$–$C_{30}$-hydrocarbon radical in which one or more, non-neighboring methylene units may be replaced by groups —O—, —CO—, —COO—, —OCO— or —OCOO—, —S—, —NH— or —N—$C_1$–$C_{20}$-alkyl and in which one or more, non-neighboring methine units may be replaced by groups —N=, —N=N— or —P=, and M denotes hydrogen, an alkali metal ion, an alkaline earth metal ion, or an ammonium ion, where in each case 2 radicals which are selected from the pairs $R^1$ and $R^2$, $R^3$ and $R^4$ and $R^1$ and $R^3$ can be linked to one another to form a cyclic structure.

The process is a retroaldolization. Carbonyl compounds of the general formula (2) can be obtained by the process in very high yields of up to or greater than 90% and in very high purities, in a simple manner, and simultaneously with very good space-time yields and hence high cost-efficiency.

The $C_1$–$C_{30}$-hydrocarbon radicals for $R^1$, $R^2$, $R^3$ and $R^4$ are preferably linear, branched or cyclic $C_1$–$C_{20}$-alkyl, $C_3$–$C_{20}$-alkoxycarbonylalkyl, $C_2$–$C_{20}$-alkenyl, $C_5$–$C_{20}$-acetalalkenyl or $C_3$–$C_{20}$-alkylcarbonyloxyalkyl radicals which may be substituted by F, Cl, Br, I, CN and $C_1$–$C_8$-alkoxy radicals and in which methylene units may be replaced by —O—, —S—, —NH— or —N—$C_1$–$C_{20}$-alkyl; aryl, aralkyl, alkaryl, aralkenyl or alkenylaryl radicals in which one or more methine units may be replaced by groups —N—, —N=N— or —P=, and methylene units by —O—, —S—, —NH— or —N—$C_1$–$C_{20}$-alkyl, and which may be substituted by F, Cl, Br, I, CN and $C_1$–$C_{10}$-alkoxy radicals and on the ring by $C_1$–$C_{10}$-alkyl radicals.

The halogen radicals $R^3$ and $R^4$ are preferably F and Cl.

The $C_1$–$C_{20}$-alkyl radicals for —N—$C_1$–$C_{20}$-alkyl in the meanings of $R^x$ may be branched, straight-chain or cyclic. Linear $C_1$–$C_{10}$-alkyl radicals are preferred.

The β-hydroxycarboxylic acids of the general formula (2) or their salts are used in the form of liquids or solids, optionally dissolved in a hydroxyl-free solvent.

Preferred hydroxyl-free solvents are aprotic solvents, in particular ethers, hydrocarbons and hydrocarbon-substituted silanes and siloxanes. Suitable ethers are mono- and polyethers, preferably symmetrical and asymmetrical di-$C_1$–$C_{10}$-hydrocarbon ethers, for example dibutyl ether, tetrahydrofuran, dihexyl ether, diphenyl ether, anisole or phenetole, or cyclic ethers, such as coumarone and tetrahydrofuran. Examples of polyethers are polyethylene glycol dimethyl ether and polyethylene glycol diethyl ether.

Preferred aromatic or aliphatic hydrocarbons are $C_1$–$C_{20}$-hydrocarbons and mixtures thereof, such as toluene, ethylbenzene, propylbenzene, isopropylbenzene, butylbenzene, xylene, xylene isomer mixtures, trimethylbenzene, octane, isooctane, nonane, nonane fractions, cycloheptane, cyclooctane, dimethylcyclohexane, ethylcyclohexane, propylcyclohexane, butylcyclohexane, petroleum benzine, and paraffin.

Hydrocarbon-substituted silanes and siloxanes are hydrocarbons in which one or more methylene groups may also be replaced by dialkylsilyl or dialkylsilyloxy groups. Preferred examples are tetraethylsilane, tetrapropylsilane, tetrabutylsilane, dimethyldiphenylsilane and polydimethylsiloxane.

Solvents or solvent mixtures having a boiling point or boiling range of up to 250° C. at 0.1 MPa are preferred.

Particularly suitable Brönstedt bases are the hydroxides, methanolates, ethanolates, oxides, amides and hydrides of lithium, sodium, potassium, magnesium and calcium. Alkali metal and alkaline earth metal hydroxides are preferably used, in particular sodium hydroxide and potassium hydroxide. The solid alkali metal and alkaline earth metal bases are used in the form of pellets, flakes, spheres, beads, prills, microprills or in pulverulent form, preferably in pulverulent form and as prills or microprills.

The process is preferably carried out at temperatures of from 50 to 300° C., in particular at from 100 to 250° C. During the reaction, the temperature is maintained at the desired value. Optionally, the upper temperature limit may be restricted by the boiling point of the inert solvent used, such as, for example, di-n-butyl ether (b.p.: 140–143° C.), nonane fraction (b.p.: 148–153° C.) or xylene isomer mixture (b.p.: 137–143° C.).

The process according to the invention can be carried out, for example, either by heating the mixture of base, hydroxycarboxylic acid of the general formula (2) and solvent to the desired temperature or first heating the mixture of base and solvent to the desired temperature and then adding the hydroxycarboxylic acid of the general formula (2). It is also possible first to heat the hydroxycarboxylic acid of the general formula (2) and solvent to the desired temperature and then to add the base. The carbonyl compound of the general formula (1) which is formed by cleavage of the hydroxycarboxylic acid is then isolated.

The hydroxycarboxylic acid of the general formula (2) can also be used in the form of its alkali metal, alkaline earth metal or ammonium salt.

The resulting carbonyl compound of the general formula (1) can preferably be obtained and isolated by distillation, extraction or crystallization or by means of chromatographic methods.

In order to obtain and isolate the resulting carbonyl compounds of the general formula (1), water or a mineral acid, in concentrated form or in the form of a dilute aqueous solution, and optionally a water-immiscible organic solvent for better phase separation, are added to the reaction mixture after the end of the reaction, optionally with cooling to temperatures of from 0° C. to 150° C., and the carbonyl compound is obtained and isolated by distillation, extraction or crystallization or by means of chromatographic methods. Alternatively, the reaction mixture can also be added to an acid (inverse neutralization). It is also possible to obtain and to isolate the carbonyl compounds of the general formula (1) after the end of the reaction from the reaction mixture by distillation, extraction or crystallization or by means of chromatographic methods, without further work-up of the reaction mixture, optionally in an aqueous medium.

In the isolation of the carbonyl compounds of the general formula (1), the solvent used can, in most cases, be recovered virtually quantitatively, which makes the process very economical, particularly when carried out on an industrial scale.

The cleavage of the hydroxycarboxylic acids of the general formula (2) can also be carried out in the presence of a high-boiling solvent, and the lower-boiling carbonyl compounds of the general formula (1) which are formed by cleavage during the reaction can immediately be collected and isolated, for example by distillation, optionally together with an entraining agent and optionally under reduced pressure of from 0.01 to 1 000 mbar.

It has proven suitable to react the hydroxycarboxylic acid of the general formula (2) with the base in the molar ratio of 1:(1 to 10), in particular 1:(1 to 3). The concentration of the hydroxycarboxylic acid of the general formula (2) in the hydroxyl-free solvent is usually from 5 to 90% by weight, in particular from 10 to 70% by weight, preferably from 15 to 50% by weight.

The pressure range of the reaction is not critical and may be varied within wide limits. The pressure is usually from 0.00001 to 20 bar, and the reaction is preferably carried out at from 0.0001 bar to atmospheric pressure.

The reaction can be carried out continuously or batchwise. A continuous reaction procedure is possible in particular with the use of a high-boiling solvent, the lower-boiling carbonyl compounds of the general formula (1) which are formed by cleavage during the reaction immediately being collected and isolated, for example by distillation, optionally under reduced pressure, preferably at from 0.01 to 1 000 mbar. In the case of a continuous reaction procedure, the hydroxycarboxylic acid of the general formula (2) can be metered in continuously. In the case of a continuous reaction procedure, the base is used in excess.

The advantage of the process according to the invention over the previously known methods is that the cleavage of the hydroxycarboxylic acids of the general formula (2), in the presence of the abovementioned bases and in particular in the presence of a hydroxyl-free solvent, takes place very rapidly with high conversion, in many cases virtually quantitatively and therefore with high yields and simultaneously very high purity of the isolated carbonyl compounds of the general formula (1). In most cases, the cleavage proceeds with unexpectedly short reaction times of from 30 min to 4 h, which makes the reaction very economical, particularly when carried out on an industrial scale, owing to very high space-time yields.

In addition, the cleavage of the hydroxycarboxylic acids of the general formula (2) takes place in most cases with very high yields of the isolated carbonyl compounds of the general formula (1) with only a small excess of from 1.5 to 3 equivalents, based on the hydroxycarboxylic acid, of the base used, which makes the reaction very economical particularly when carried out on an industrial scale.

It was not to be foreseen that the cleavage of the hydroxycarboxylic acids of the general formula (2) under the conditions according to the invention, in particular with the use of a hydroxyl-free solvent, would take place very rapidly and with a very high conversion and that it would be possible to isolate the carbonyl compounds of the general formula (2) in very high yields.

All the above symbols of the above formulae have their meanings in each case independently of one another.

In the examples below, all quantity and percentage data are based on weight, all pressures are 0.10 MPa (abs.) and all temperatures are 20° C., unless stated otherwise.

EXAMPLE 1

Preparation of 1-phenylhexan-3-one 6.8 g of sodium hydroxide prills (170 mmol) in 100 ml of a nonane fraction (b.p.: 148–153° C.) were initially introduced at room temperature into a three-necked flask having a reflux condenser, internal thermometer and stirrer. After 20 g of 3-hydroxy-3-(2'-phenylethyl)hexanoic acid (85 mmol), prepared according to K. S. Fors, J. R. Gage, R. F. Heier, R. C. Kelly, W. R. Perrault and N. Wicnienski, J. ORG. CHEM. 63, 7348 (1998), had been added, the mixture was heated to 155° C., a clear solution initially forming. The mixture was stirred for 2 h at 150° C., a colorless precipitate forming. The mixture was then allowed to cool to 20° C., hydrolyzed with 80 ml of 2 N hydrochloric acid (pH 1) and stirred for 15 min and the organic phase separated. The organic phase was washed with 30 ml of saturated sodium bicarbonate solution. After phase separation, drying was effected over sodium sulfate and the solvent was distilled off under reduced pressure (>90% of the solvent was recovered). 1-phenylhexan-3-one was obtained in a yield of 13.6 g (91% of theory) with a boiling point of 134° C. (13 mbar).

Analogous preparation in the solvents di-n-butyl ether (b.p.: 140–143° C.) and xylene isomer mixture (b.p.: 137–143° C.) gave 1-phenylhexan-3-one in yields of 12.5 g and 13.3 g (83 and 89% of theory, respectively).

EXAMPLE 2

Preparation of 1-phenylhexan-3-one 8.5 g of sodium hydroxide prills (213 mmol) in 100 ml of polyethylene glycol 1000 dimethyl ether (m.p.: 42° C.) were initially introduced at room temperature into a 3-necked flask having a dropping funnel, internal thermometer and stirrer. After 25 g of 3-hydroxy-3-(2'-phenylethyl)hexanoic acid (106 mmol), prepared according to K. S. Fors, J. R. Gage, R. F. Heier, R. C. Kelly, W. R. Perrault and N. Wicnienski, J. ORG. CHEM. 63, 7348 (1998), had been added, the mixture was heated to 80° C. for 10 min and then to 150° C. Thereafter, the pressure was reduced to 2.5 mbar and the mixture was stirred for 2 h at 150° C. and a pressure of 2.5 mbar, 1-phenylhexan-3-one formed by cleavage being collected in a cooled receiver. The 1-phenylhexan-3-one collected in the receiver was obtained, after washing with 20 ml of water, in a yield of 12.1 g (81% of theory) with a boiling point of 133° C. (13 mbar).

EXAMPLE 3

(Comparative Example)

Preparation of 1-phenylhexan-3-one according to D. Ivanoff, BULL. SOC. CHIM. France 36, 321 (1933) and C. S. Rondestvedt and M. E. Rowley, J. AM. CHEM. SOC. 78, 3804 (1956).

6.8 g of sodium hydroxide prills (170 mmol) in 100 ml of 1-butanol were initially introduced at room temperature into a three-necked flask having a reflux condenser, internal thermometer and stirrer. After 20 g of 3-hydroxy-3-(2'-phenylethyl)hexanoic acid (85 mmol), prepared according to K. S. Fors, J. R. Gage, R. F. Heier, R. C. Kelly, W. R. Perrault and N. Wicnienski, J. ORG. CHEM. 63, 7348 (1998), had been added, the mixture was heated to 115° C.. The mixture was stirred for 2 h at 115° C., cooled to 20° C. and hydrolyzed with 80 ml of 2 N hydrochloric acid (pH: 1) and the mixture was stirred for 15 min. After phase separation, the organic phase was washed with 30 ml of saturated sodium bicarbonate solution. After phase separation, drying was effected over sodium sulfate and the solvent was distilled off under reduced pressure. The conversion of 1-phenylhexan-3-one is 9% of theory.

What is claimed is:

1. A process for the preparation of a carbonyl compound of the general formula (1)

$$R^1R^2C=O \qquad (1),$$

comprising cleaving a β-hydroxycarboxylic acid or its salt of the general formula (2)

$$R^1R^2C(OH)-CR^3R^4-COOM \qquad (2),$$

in the presence of a Brönstedt base which is selected from the group consisting of hydroxides, alkanolates, oxides, amides, and hydrides of the alkali metals and alkaline earth metals, and mixtures of these Brönstedt bases, and in the presence of a hydroxyl-free solvent, where $R^1$ denotes an optionally halogen- or cyano-substituted $C_1$–$C_{30}$-hydrocarbon radical in which one or more, non-neighboring methylene units may be replaced by groups —O—, —CO—, —COO—, —OCO— or —OCOO—, —S— or —NR$^x$— and in which one or more, non-neighboring methine units may be replaced by groups —N=, —N=N— or —P=, $R^2$ denotes hydrogen or an optionally halogen- or cyano-substituted $C_1$–$C_{30}$-hydrocarbon radical in which one or more, non-neighboring methylene units may be replaced by groups —O—, —CO—, —COO—, —OCO— or —OCOO—, —S— or —NR$^x$— and in which one or more, non-neighboring methine units may be replaced by groups —N=, —N=N— or —P=, $R^3$ and $R^4$ denote hydrogen, halogen or an optionally halogen- or cyano-substituted $C_1$–$C_{30}$-hydrocarbon radical in which one or more, non-neighboring methylene units may be replaced by groups —O—, —CO—, —COO—, —OCO— or —OCOO—, —S— or —NR$^x$— and in which one or more, non-neighboring methine units may be replaced by groups —N=, —N=N— or —P=, $R^x$ denotes hydrogen or an optionally halogen- or cyano-substituted $C_1$–$C_{30}$-hydrocarbon radical in which one or more, non-neighboring methylene units may be replaced by groups —O—, —CO—, —COO—, —OCO— or —OCOO—, —S—, —NH— or —N—$C_1$–$C_{20}$-alkyl and in which one or more, non-neighboring methine units may be replaced by groups —N=, —N=N— or —P=, and M denotes hydrogen, an alkali metal ion, an alkaline earth metal ion or an ammonium ion, where in each case 2 radicals which are selected from the pairs $R^1$ and $R^2$, $R^3$ and $R^4$ and $R^1$ and $R^3$ can be linked to one another.

2. The process of claim 1, wherein the hydroxyl-free solvent is selected from ethers, hydrocarbons and hydrocarbon-substituted silanes and siloxanes.

3. The process of claim 1, wherein the Brönstedt base is selected from alkali metal and alkaline earth metal hydroxides.

4. The process of claim 2, wherein the Brönstedt base is selected from alkali metal and alkaline earth metal hydroxides.

5. The process of claim 1, wherein the hydroxycarboxylic acid of the general formula (2) is reacted with the Brönstedt base in the molar ratio 1:(1 to 10).

6. The process of claim 2, wherein the hydroxycarboxylic acid of the general formula (2) is reacted with the Brönstedt base in the molar ratio 1:(1 to 10).

7. The process of claim 3, wherein the hydroxycarboxylic acid of the general formula (2) is reacted with the Brönstedt base in the molar ratio 1:(1 to 10).

8. The process of claim 1, wherein said hydroxyl-free solvent has a boiling point lower than said carbonyl compound (1) at the pressure at which the reaction takes place.

9. The process of claim 1, wherein said hydroxyl-free solvent has a boiling point higher than said carbonyl compound (1) at the pressure at which the reaction takes place.

10. The process of claim 1, further comprising neutralizing the reaction mixture obtained from the process of cleaving by adding aqueous acid.

11. The process of claim 10, wherein a water-miscible organic solvent is added prior to, concurrently, or subsequent to said step of neutralizing.

12. The process of claim 1 wherein said Brönstedt base comprises sodium hydroxide, potassium hydroxide, or a mixture thereof.

13. The process of claim 1 wherein said Brönstedt base comprises a Brönstedt base selected from the group consisting of potassium methoxide, sodium methoxide, potassium ethoxide, sodium ethoxide, and mixtures thereof.

14. The process of claim 1 wherein said Brönstedt base comprises one or more amide(s) of lithium, sodium, potassium, magnesium, or calcium.

15. The process of claim 1 wherein said aprotic solvent comprises an aromatic or aliphatic hydrocarbon or mixture thereof.

16. The process of claim 3 wherein said aprotic solvent comprises an aromatic or aliphatic hydrocarbon or mixture thereof.

17. The process of claim 12 wherein said aprotic solvent comprises an aromatic or aliphatic hydrocarbon or mixture thereof.

18. The process of claim 1 wherein said aprotic solvent comprises a polyether.

19. The process of claim 3 wherein said aprotic solvent comprises a polyether.

20. The process of claim 1 wherein said aprotic solvent comprises a hydrocarbon-substituted silane or a hydrocarbon-substituted siloxane.

\* \* \* \* \*